(12) United States Patent
Huang et al.

(10) Patent No.: US 8,947,516 B2
(45) Date of Patent: Feb. 3, 2015

(54) HIGH-RESOLUTION 3D IMAGING OF SINGLE SEMICONDUCTOR NANOCRYSTALS

(75) Inventors: Hao Huang, New York, NY (US); Yu Yao, Cambridge, MA (US); C. Forbes Dewey, Boston, MA (US); Moungi G. Bawendi, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 723 days.

(21) Appl. No.: 12/680,150

(22) PCT Filed: Sep. 26, 2008

(86) PCT No.: PCT/US2008/077874
§ 371 (c)(1),
(2), (4) Date: Oct. 21, 2010

(87) PCT Pub. No.: WO2009/082523
PCT Pub. Date: Jul. 2, 2009

(65) Prior Publication Data
US 2011/0037846 A1     Feb. 17, 2011

Related U.S. Application Data

(60) Provisional application No. 60/975,319, filed on Sep. 26, 2007.

(51) Int. Cl.
*H04N 7/18*     (2006.01)
*G01N 21/64*    (2006.01)

(52) U.S. Cl.
CPC ........ *G01N 21/6458* (2013.01); *G01N 21/6428* (2013.01); *G01N 2021/6441* (2013.01)

USPC ........... 348/79; 250/231.13; 250/458.1; 252/301.36; 252/301.4 R; 252/301.6 S; 356/73; 428/379; 428/403; 428/548; 435/6.11; 435/6.12; 435/6.14; 435/7.1; 436/92; 436/524; 438/25; 438/689

(58) Field of Classification Search
CPC .......... G01N 21/6428; G01N 21/6458; G01N 21/25; B82Y 15/00; G01D 5/268
USPC ........ 348/79; 435/6, 7.5; 514/260.1; 428/403
IPC ........................................................ H04N 7/18
See application file for complete search history.

(56) References Cited

U.S. PATENT DOCUMENTS

| | | |
|---|---|---|
| 6,251,303 B1 | 6/2001 | Bawendi et al. |
| 6,306,610 B1 | 10/2001 | Bawendi et al. |
| 6,319,426 B1 | 11/2001 | Bawendi et al. |
| 6,322,901 B1 | 11/2001 | Bawendi et al. |
| 6,576,291 B2 | 6/2003 | Bawendi et al. |
| 6,921,496 B2 | 7/2005 | Anderson et al. |

(Continued)

OTHER PUBLICATIONS

Toprak, Erdal, et al. "Three-dimensional particle tracking via bifocal imaging." Nano letters 7.7 (2007): 2043-2045.*

(Continued)

*Primary Examiner* — Jay Patel
*Assistant Examiner* — Neil Mikeska
(74) *Attorney, Agent, or Firm* — Steptoe & Johnson LLP

(57) ABSTRACT

A method of imaging microscopic objects includes determining the relative depths of two or more semiconductor nanocrystals by analyzing images of the semiconductor nanocrystals at varying z-displacements.

12 Claims, 16 Drawing Sheets

(56) References Cited

U.S. PATENT DOCUMENTS

| | | |
|---|---|---|
| 7,160,613 B2 | 1/2007 | Bawendi et al. |
| 7,190,870 B2 | 3/2007 | Sundar et al. |
| 7,229,690 B2 | 6/2007 | Chan et al. |
| 2003/0113709 A1* | 6/2003 | Alivisatos et al. ............... 435/4 |
| 2004/0021091 A1 | 2/2004 | Ghosh et al. |
| 2004/0110002 A1 | 6/2004 | Kim et al. |
| 2005/0059681 A1* | 3/2005 | Cremer et al. ............. 514/260.1 |
| 2005/0123979 A1* | 6/2005 | Weiss et al. ........................ 435/6 |
| 2005/0211885 A1* | 9/2005 | Tobiason et al. ......... 250/231.13 |
| 2006/0172133 A1* | 8/2006 | Naasani ....................... 428/403 |
| 2006/0216759 A1* | 9/2006 | Naasani ........................ 435/7.5 |
| 2006/0244963 A1* | 11/2006 | Empedocles et al. ......... 356/326 |
| 2006/0280680 A1* | 12/2006 | Li ................................. 424/1.49 |
| 2007/0215815 A1 | 9/2007 | Wohland et al. |
| 2010/0155668 A1* | 6/2010 | Weiss et al. .............. 252/301.36 |
| 2011/0059467 A1* | 3/2011 | Ting et al. .................... 435/7.21 |
| 2012/0315218 A9* | 12/2012 | Chen ............................. 424/9.1 |

OTHER PUBLICATIONS

Neely, L.A., et al., (2006). *Nat. Methods* 3, 41-46.
Agrawal, A., et al. (2006). *Anal. Chem.* 78, 1061-1070.
Gao, X., et al. (2005). *Curr.Opin.Biotechnol.* 16, 63-72.
M. Speidel, A. Jonas, and F. E., *Opt. Lett.* 28, 69 (2003).
M. Jonas, Y. Yao, P. T. C. So, and C. F. Dewey, IEEE Transactions on Nanobioscience 5, 246 (2006).
Yildiz, A. et al., *Science* 300, 2061-2065 (2003).
Thompson, R.E. et al., *Biophys J.* 82, 2775-2783, 2002.
Murray, C.B., et al., *J. Am. Chem. Soc.* 1993, 115, 8706.
Mikulec, F., Ph.D. Thesis, MIT, Cambridge, 1999.
Peng, X., et al., *J. Am. Chem. Soc.* 1997, 119, 7019.
Dabbousi, B.O., et al., *J. Phys. Chem. B* 1997, 101, 9463.
Cao, Y. W. and Banin, U. *Angew. Chem. Int. Edit.* 1999, 38, 3692.
Wang, Y.A., et al., 2002 *J. Am. Chem. Soc* 124, 2293.

* cited by examiner

HIGH-RESOLUTION 3D IMAGING OF SINGLE SEMICONDUCTOR NANOCRYSTALS

CLAIM OF PRIORITY

This application claims priority under 35 USC 371 to International Application No. PCT/US 2008/077874, filed on Sep. 26, 2008, which claims priority to U.S. Provisional Application Ser. No. 60/975,319, filed Sep. 26, 2007, each of which is incorporated by reference in its entirety.

FEDERALLY SPONSORED RESEARCH OR DEVELOPMENT

This invention was made with government support under Grant No. CA 119349 awarded by the National Institutes of Health. The government has certain rights in this invention.

TECHNICAL FIELD

The invention relates to high resolution 3D imaging of single semiconductor nanocrystals.

BACKGROUND

Semiconductor nanocrystals are photostable fluorophores with narrow emission spectra tunable through visible and near-infrared wavelengths, large molar extinction coefficients, and high quantum yields. These properties make semiconductor nanocrystals powerful tools for labeling and optical sensing in biological, biomedical, and environmental contexts. The exceptional brightness and photostability of semiconductor nanocrystals give them great potential for analyzing biological events at the single molecule level. However, current nanocrystals designed for cellular labeling applications suffer a tradeoff between size, non-specific binding, and derivatizability.

Nanocrystals generally include an inorganic nanoparticle that is surrounded by a layer of organic ligands. This organic ligand shell is critical to the nanocrystals for processing, binding to specific other moieties, and incorporation into various substrates. Nanocrystals can be stored in their growth solution, which contains a large excess of ligands such as alkyl phosphines and alkyl phosphine oxides, for long periods without noticeable degradation. For most applications, particularly aqueous applications, nanocrystals must be processed outside of their growth solution and transferred into various chemical environments. However, nanocrystals often lose their high fluorescence or become irreversibly aggregated when removed from their growth solution.

SUMMARY

Single-particle tracking can give unprecedented understanding of the motion of cell surface proteins, free from the simplification of ensemble averaging. However, single-particle tracking is complicated by fluorophore photobleaching, probe multivalency, the size of the labeling probe, and dissociation of the probe from the target. Semiconductor nanocrystals have the intrinsic advantages for single particle tracking of brightness and photostability.

A lens-based optical microscope can provide a resolution only close to half of the wavelength of light, on the order of hundred of nanometers for visible light. A nanocrystal-based tracking method which provides nanometer spatial resolution (e.g., on the order of 10 nm) in three dimensions. The tracking method can be used in tracking objects and structures (for example, biological objects and structures) on a micro- or nano-meter scale. The method to three dimensionally map a ~350 nm thick polysaccharide layer called the glycocalyx on bovine aortic endothelial cells, and to study the mechanical properties of the polysaccharide layer under flow.

In one aspect, a method of imaging a microscopic object includes arranging a microscopic object associated with at least a first and a second semiconductor nanocrystal in the optical field of an optical microscope, recording a first fluorescence image of the first and second semiconductor nanocrystals at a first focal depth, recording a second fluorescence image of the first and second semiconductor nanocrystals at a second focal depth different from the first focal depth, and calculating the relative depths of the first and second semiconductor nanocrystals based at least in part on the first and second fluorescence images.

Calculating the relative depths of the first and second semiconductor nanocrystals can include measuring a radius of the first semiconductor nanocrystal as it appears in each of the first and second fluorescence images. Measuring the radius can include measuring a radius of a local intensity maximum. When there are multiple local intensity maxima, the local intensity maximum having the greatest radius can be chosen. Measuring the radius can include measuring a radius at a plurality of different angles. Measuring the radius can include determining a radial intensity profile. Determining the radial intensity profile can include calculating an integrated radial intensity profile for a plurality of different angles. The method can include fitting the radial intensity profile with one or more Gaussian curves.

The method can include correlating the measured radius of the first semiconductor nanocrystal with the relative depth of the first semiconductor nanocrystal. The method can include determining relative three-dimensional coordinates of the first and second semiconductor nanocrystals based at least in part on the first and second fluorescence images. The method can include determining a three-dimensional shape of the object based at least in part on the relative three-dimensional coordinates of the first and second semiconductor nanocrystals.

The object can include a biological structure. The biological structure can include a cell. The first semiconductor nanocrystal can be associated with a moiety having a specific affinity for a biomolecule.

The method can include tracking the location of at least one semiconductor nanocrystal as a function of time. Tracking the location can include determining three-dimensional coordinates for the semiconductor nanocrystal.

In another aspect, a method of determining the location of a nanocrystal in three dimensions includes recording a fluorescence image of a semiconductor nanocrystal, determining x- and y-coordinates from the center of the nanocrystal image, and determining a z-coordinate from the radius of the nanocrystal image.

The x-, y- and z-coordinates each individually can have a precision of ±15 nm or less, or a precision of ±10 nm or less. In some embodiments, at least one of the x- and y-coordinates can have a precision of ±5 nm or less, and the z-coordinate can have a precision of ±10 nm or less.

Determining a z-coordinate from the radius of the nanocrystal image can include determining a radial intensity profile. Determining the radial intensity profile can include calculating an integrated radial intensity profile for a plurality of different angles. The method can include fitting the radial intensity profile with one or more Gaussian curves.

Recording a fluorescence image of a semiconductor nanocrystal can include recording fluorescence images of a plurality of semiconductor nanocrystals in a single fluorescence image.

Recording a fluorescence image of a semiconductor nanocrystal can include recording a first fluorescence image of a field at a first emission wavelength or range of wavelengths, and recording a second fluorescence image of the field at a second emission wavelength or range of wavelengths.

The method can include moving the field in the z-direction, and repeating the steps of recording a first image of the field at a first emission wavelength or range of wavelengths, and recording a second image of the field at a second emission wavelength or range of wavelengths.

In another aspect, an apparatus for imaging a microscopic object includes an objective lens configured to image a microscopic object arranged on a nanopositioner stage, a light source configured to simultaneously excite fluorescence from at least a first and a second semiconductor nanocrystal associated with the microscopic object, and a camera configured to record a first fluorescence image of the first and second semiconductor nanocrystals at a first focal depth and to record a second fluorescence image of the first and second semiconductor nanocrystals at a second focal depth different from the first focal depth.

The apparatus can include a computer system configured to calculate the relative depths of the first and second semiconductor nanocrystals by measuring a radius of the first semiconductor nanocrystal as it appears in each of the first and second fluorescence images. The computer system can be further configured to measure the radius by calculating an integrated radial intensity profile for a plurality of different angles and fitting the radial intensity profile with one or more Gaussian curves.

Other features, objects, and advantages of the invention will be apparent from the description and drawings, and from the claims.

DETAILED DESCRIPTION

Figure 1:
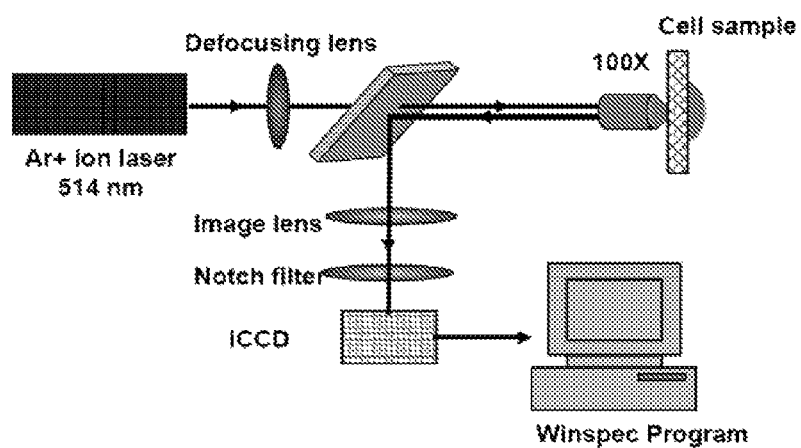
FIG. 1 is schematic depiction of an epifluorescence microscope system.

One goal of cellular imaging is to observe in living cells the movement of single biomolecules. Single molecules imaging in vitro has proved its ability to give the ultimate in sensitivity, detecting low abundance biomolecules such as miRNA or virus particles (see, e.g., Neely, L. A., et al., (2006). *Nat. Methods* 3, 41-46; and Agrawal, A., et al. (2006). *Anal. Chem.* 78, 1061-1070, each of which is incorporated by reference in its Semiconductor nanocrystals provide certain advantages in tracking the movement of single particles. Single semiconductor nanocrystals are bright enough to be seen easily on a wide field fluorescence microscope, without the need for TIRF, and are extremely photostable (Gao, X., et al. (2005). *Curr. Opin. Biotechnol.* 16, 63-72, which is incorporated by reference in its entirety).

Ordinary light microscopy is limited to resolving objects a few hundred nanometers in size. Defocused imaging can locate the depth of particles with high resolution. See, e.g., M. Speidel, A. Jonas, and F. E., *Opt. Lett.* 28, 69 (2003) ("Speidel"), which is incorporated by reference in its entirety. Briefly, the apparent radius of a point object, when in focus, can be described by:

$$r \sim 0.61 \lambda / NA$$

where NA is the numerical aperture of the objective lens. As the object undergoes displacement in the z-direction (i.e., orthogonal to the focal plane), the image of the object becomes defocused. When the object is an emissive light source, and is small compared to the wavelength of the emitted light, interference rings become apparent as the z displacement increases. As described in Speidel, the z displacement is linearly correlated with radius of the outermost interference ring, $r_0$.

In part due to their small size, microscopic imaging of semiconductor nanocrystals can provide very high effective resolution: the center of the interference rings can be accurately determined by two-dimensional Gaussian fitting, providing sub-diffraction limited resolution within the imaging plane. Thus, isolated emitters can be located in the focal plane of a microscope with much higher resolution than what conventional design rules would suggest, as well as being located in the z-direction. In one example, the trajectory of a single nanocrystal could be tracked with approximately 4 nm accuracy. See M. Jonas, Y. Yao, P. T. C. So, and C. F. Dewey, IEEE Transactions on Nanobioscience 5, 246 (2006); see also Yildiz, A. et al., *Science* 300, 2061-2065 (2003), each of which is incorporated by reference in its entirety. For stationary nanocrystals, an x,y precision of ~1.3 nm has been demonstrated (Thompson, R. E. et al., *Biophys J.* 82, 2775-2783, 2002, which is incorporated by reference in its entirety).

The images and data presented in FIGS. 2-6 were recorded for nanocrystals that had been spin-coated onto a piece of smooth cover glass (RMS roughness ~1 nm from atomic force microscope measurements). The λ=514 nm line of an Ar-ion laser was used as the excitation source with a typical intensity of ~20 W/cm$^2$. Images were taken using a 100× oil immersion objective (Nikon, Plan Apo, NA=1.4) and an intensified CCD Camera (Pentamax, Princeton Instruments)

with an effective pixel size of 90 nm; the actual image area captured by each pixel can vary with the post-objective magnification used.

Figure 2:
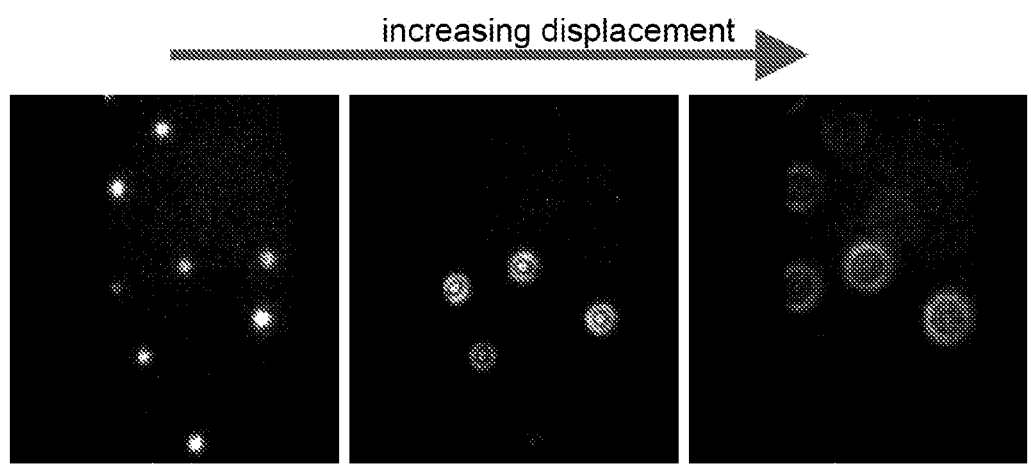
FIG. 2 are a series of fluorescence microscope images of nanocrystals at varying z-displacement.
Figure 3:
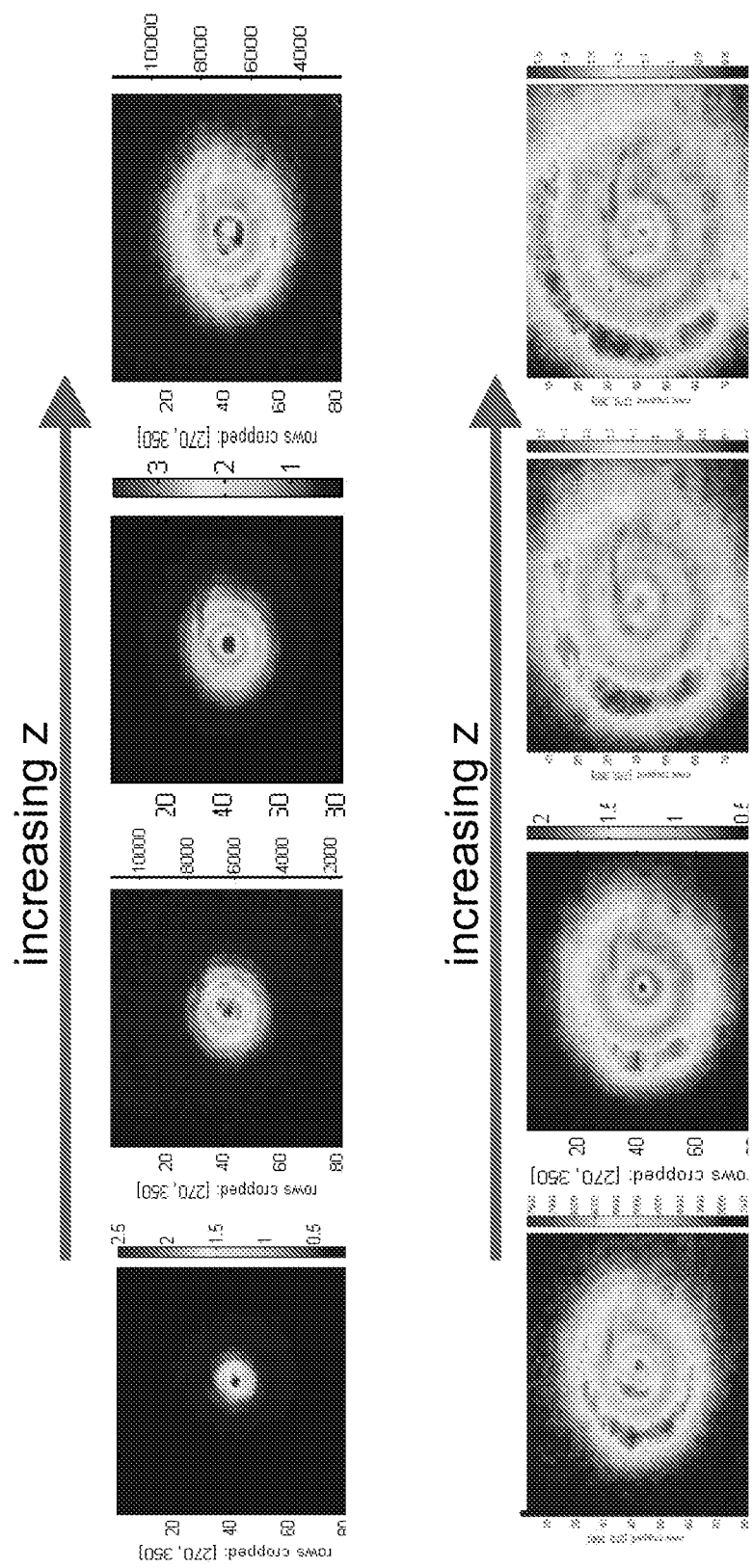
FIG. 3 are false color images of a single nanocrystal at varying z-displacements.

FIG. 2 shows fluorescence microscope images of a field of nanocrystals at different values of z-displacement. FIG. 3 shows false color images of a single semiconductor nanocrystal at different values of z-displacement. The colors indicate intensity measured at the CCD detector. When nanocrystals are in focus, the fluorescence from each individual nanocrystal appears as a bright spot. As a nanocrystal is moved away from the focal plane using a piezo driven stage, complex ring patterns form due to the diffraction of the emission from each nanocrystal.

Figure 4:
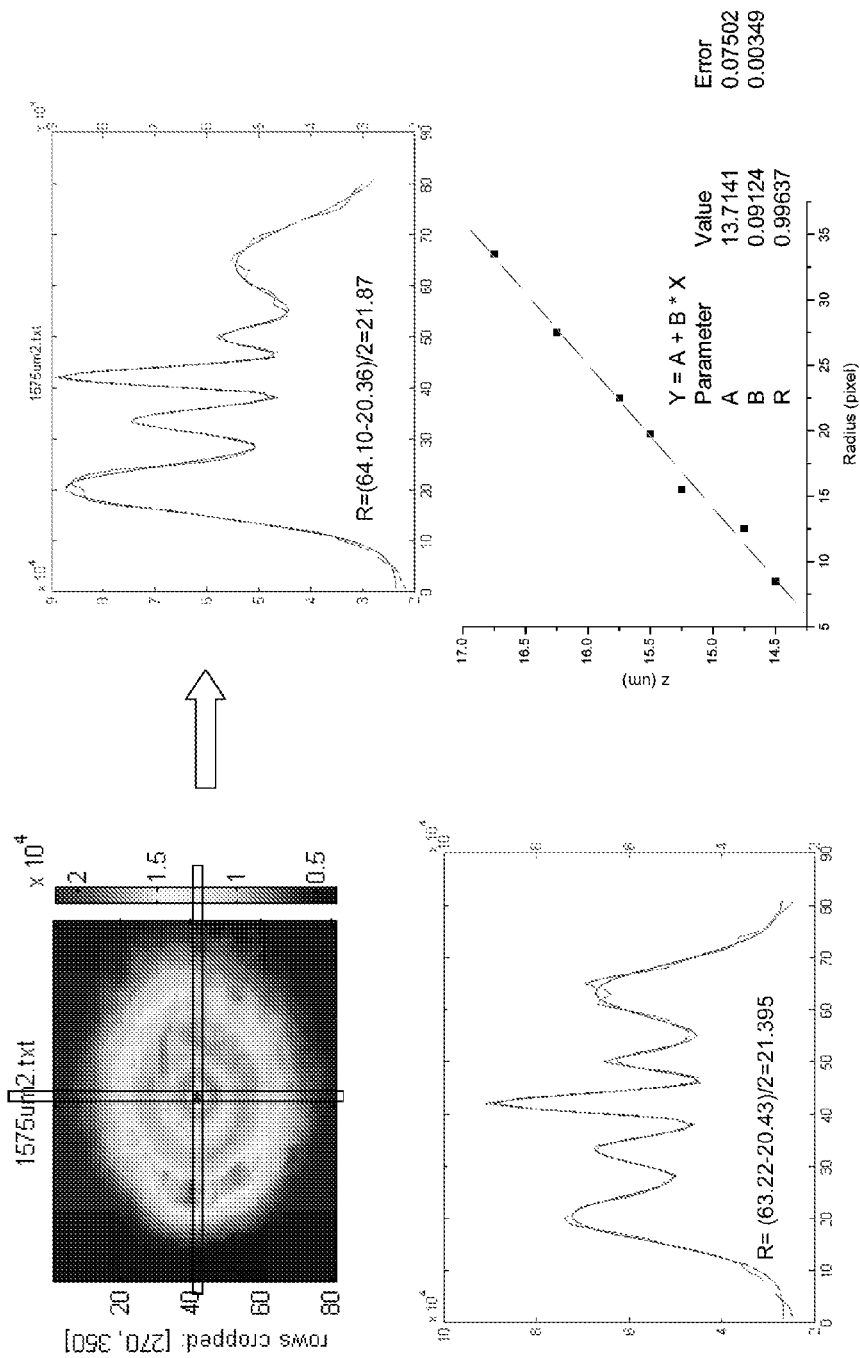
FIG. 4 illustrates a method for determining the radius of a defocused image of a nanocrystal.

FIG. 4 illustrates one method for determining the radius $r_0$ of the interference fringes. A "slice" including the center of the image is taken, and the resulting profile is fit to Gaussian curves (i.e., curves having the form $f(r)=\exp[-k(r-r_0)^2]$ are Gaussian curves). The radius $r_0$ is calculated as the distance between the peaks of the center and outermost Gaussian curves. As shown in FIG. 4, more than one "slice" can be taken for each image. The plot at lower right in FIG. 4 illustrates the linear correlation between $r_0$ and z displacement.

Figure 5:
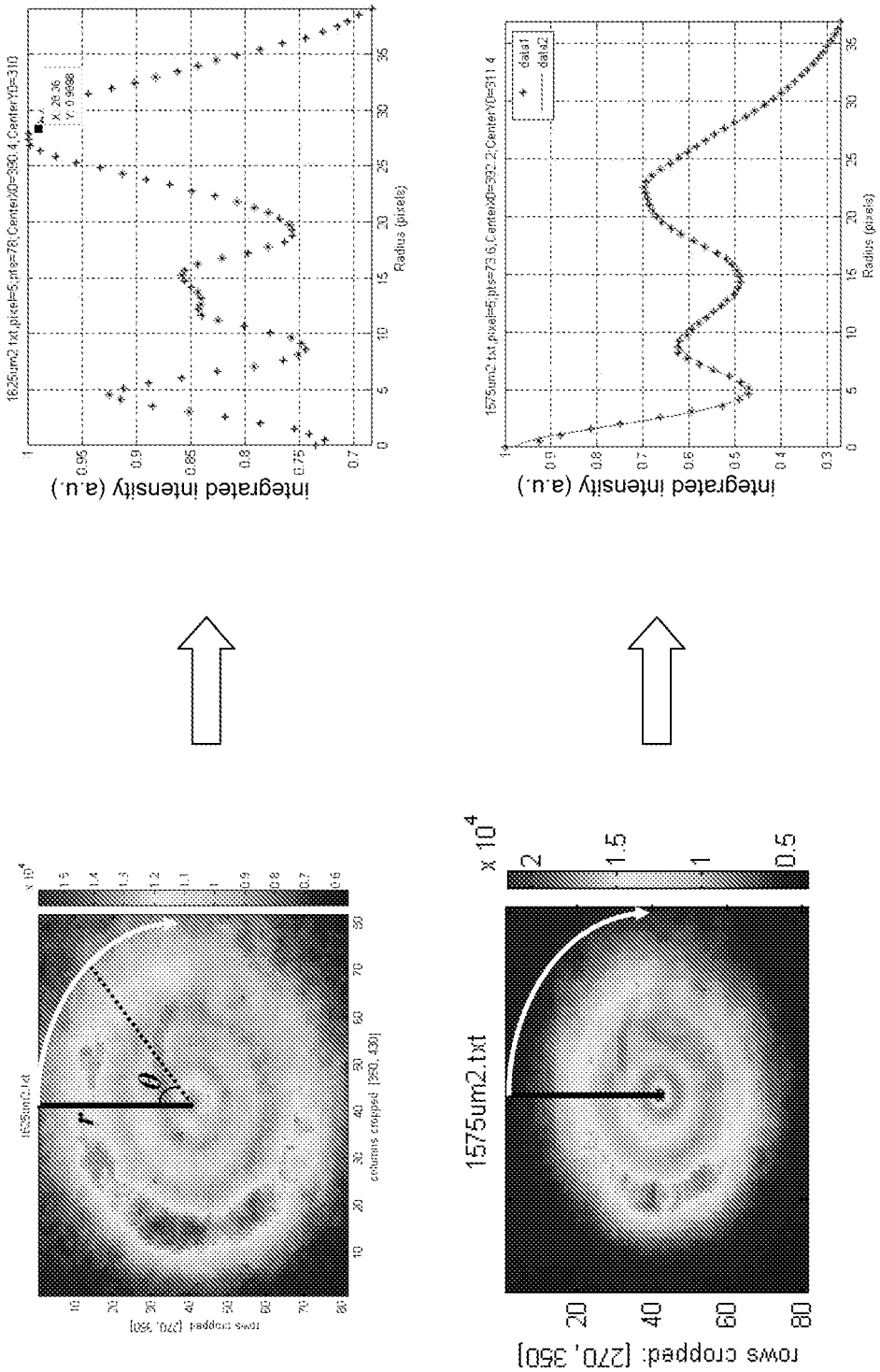
FIG. 5 illustrates a method for determining the radius $r_0$ of a defocused image of a nanocrystal.

FIG. 5 illustrates another method for determining $r_0$. The integration of photon intensity as a function of angle θ is plotted against the radial distance, and fitted to a multi-Gaussian function to calculate the center of the outermost ring, i.e., $r_0$ (fitting result shown as red curve).

Figure 6:
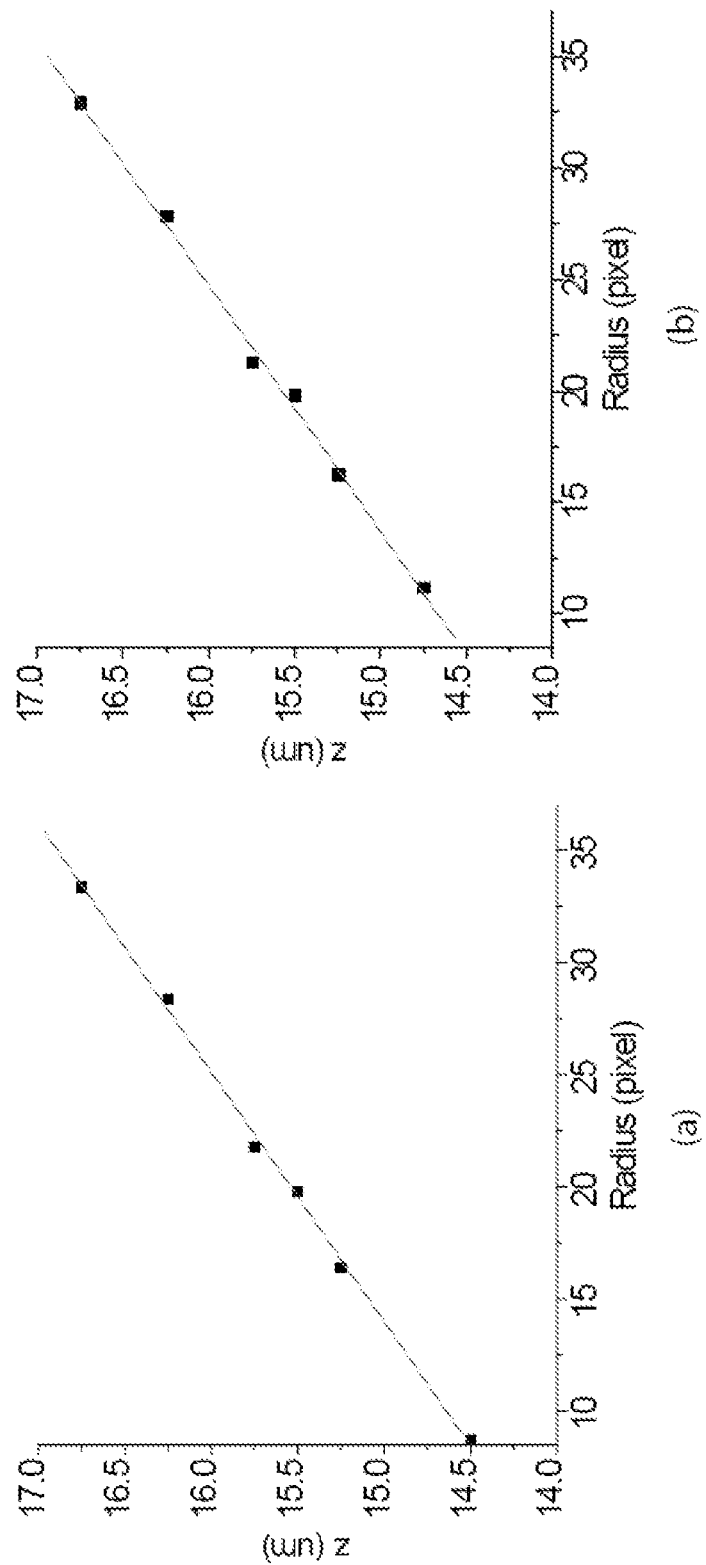
FIGS. 6A and 6B are graphs depicting the relationship between the radius $r_0$ and z-displacement for individual nanocrystals.
FIG. 6C is graph depicting measured z-displacement for nanocrystals as a function of time.

As shown in FIG. 6, the measured correlation between $r_0$ and z-displacement is linear. For the fit shown in FIG. 6, a change in $r_0$ of ~50 nm (near the pixel size of the detector) corresponds to a z-displacement of 90 nm. The resolution in z-displacement was approximately 8 nm, based the standard deviation of the measured ring sizes of several nanocrystals at the same image plane. The interpolation to zero radius for the FIG. 6A and FIG. 6B were 13.740 μm and 13.750 μm, respectively, a difference of 10 nm, consistent with nanocrystals having been deposited on a flat surface.

Figure 6C:
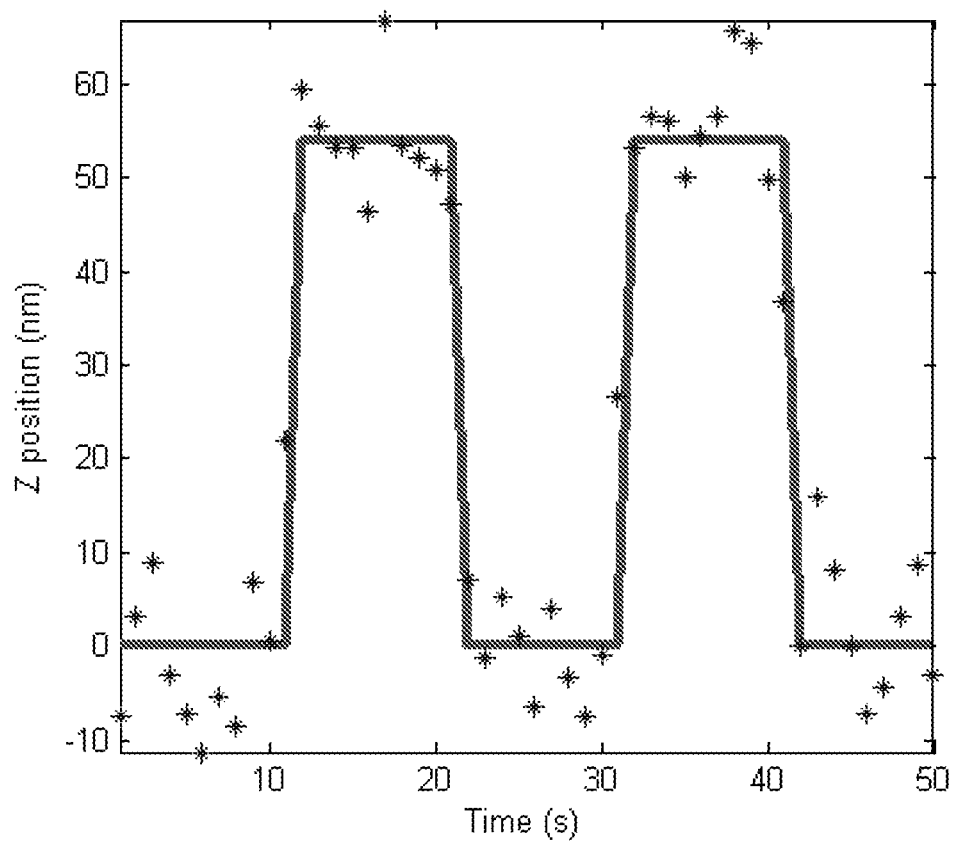

A final dynamic test was made by displacing the microscope slide vertically by 50±1 nm using a 0.1 Hz square wave motion. The results shown in FIG. 6C, illustrate the mean and standard deviation of the measured positions of a single nanocrystal with repeated realizations of the image analysis. The difference between the means of the two displacements in FIG. 6C was 54 nm, as shown by the red line. The standard deviation around each mean, taken as a measure of the repeatability of the analysis procedure on noisy images, was 9 nm.

Due to the wavelength-dependency of the diffraction pattern, nanocrystals having different emission wavelengths were calibrated separately. However, when the chromatic aberration of the imaging system was investigated (by imaging three differently-emitting nanocrystals simultaneously), the results indicated that the slopes $\Delta z/\Delta r$ were independent of wavelength. The slope $\Delta z/\Delta r$ does depend on the microscope objective.

Nanocrystal cores can be prepared by the pyrolysis of organometallic precursors in hot coordinating agents. See, for example, Murray, C. B., et al., *J. Am. Chem. Soc.* 1993, 115, 8706, and Mikulec, F., Ph.D. Thesis, MIT, Cambridge, 1999, each of which is incorporated by reference in its entirety. Growth of shell layers on the bare nanocrystal cores can be carried out by simple modifications of conventional overcoating procedures. See, for example, Peng, X., et al., *J. Am. Chem. Soc.* 1997, 119, 7019, Dabbousi, B. O., et al., *J. Phys. Chem. B* 1997, 101, 9463, and Cao, Y. W. and Banin, U. *Angew. Chem. Int. Edit.* 1999, 38, 3692, each of which is incorporated by reference in its entirety.

A coordinating agent can help control the growth of the nanocrystal. The coordinating agent is a compound having a donor lone pair that, for example, has a lone electron pair available to coordinate to a surface of the growing nanocrystal. The coordinating agent can be a solvent. A coordinating agent can stabilize the growing nanocrystal. Typical coordinating agents include alkyl phosphines, alkyl phosphine oxides, alkyl phosphonic acids, or alkyl phosphinic acids, however, other coordinating agents, such as pyridines, furans, and amines may also be suitable for the nanocrystal production. Examples of suitable coordinating agents include pyridine, tri-n-octyl phosphine (TOP) and tri-n-octyl phosphine oxide (TOPO). Technical grade TOPO can be used.

The outer surface of the nanocrystal can include a layer of compounds derived from the coordinating agent used during the growth process. The surface can be modified by repeated exposure to an excess of a competing coordinating group to form an overlayer. For example, a dispersion of nanocrystals capped with the coordinating agent used during growth can be treated with a coordinating organic compound, such as pyridine, to produce crystallites which disperse readily in pyridine, methanol, and aromatics but no longer disperse in aliphatic solvents. Such a surface exchange process can be carried out with any compound capable of coordinating to or bonding with the outer surface of the nanocrystal, including, for example, phosphines, thiols, amines and phosphates. The nanocrystal can be exposed to short chain polymers which exhibit an affinity for the surface and which terminate in a moiety having an affinity for a suspension or dispersion medium. Such affinity improves the stability of the suspension and discourages flocculation of the nanocrystal.

Monodentate alkyl phosphines and alkyl phosphine oxides passivate nanocrystals efficiently. Note that the term phosphine will refer to both phosphines and phosphine oxides below. Other conventional ligands such as thiols or phosphonic acids can be less effective than monodentate phosphines for maintaining the initial high nanocrystal luminescence over long periods. For example, the photoluminescence of nanocrystals consistently diminishes or quenches after ligand exchanges with thiols or phosphonic acid.

Ligand exchanges can be carried out by one-phase or two-phase methods. Prior to ligand exchange, nanocrystals can be precipitated from their growth solutions by addition of methanol. The supernatant solution, which includes excess coordinating agent (e.g., trioctylphosphine), can be discarded. The precipitated nanocrystals can be redispersed in hexanes. Precipitation and redispersion can be repeated until essentially all the excess coordinating agent has been separated from the nanocrystals. A one-phase process can be used when both the nanocrystals and the ligands to be introduced are soluble in the same solvent. A solution with an excess of new ligands can be mixed with the nanocrystals. The mixture can be stirred at an elevated temperature until ligand exchange is complete. The one-phase method can be used, for example, to exchange octyl-modified oligomeric phosphines or methacrylate-modified oligomeric phosphines, which are both soluble in solvents that are compatible with the nanocrystals, such as hexanes. A two-phase ligand exchange process can be preferable when the nanocrystals and the new ligands do not have a common solvent. Nanocrystals can dissolved in an organic solvent such as dichloromethane, and the new ligand can be dissolved in an aqueous solution. The nanocrystals can be transferred from the organic phase to the aqueous phase by, for example, sonication. The transfer can be monitored through absorption and emission spectroscopy. A similar two-phase ligand exchange process has been reported earlier.

See, for example, Wang, Y. A., et al., 2002 *J. Am. Chem. Soc* 124, 2293, incorporated by reference in its entirety.

The nanocrystal can be a member of a population of nanocrystals having a narrow size distribution. The nanocrystal can be a sphere, rod, disk, or other shape. The nanocrystal can include a core of a semiconductor material. The nanocrystal can include a core having the formula MX, where M is cadmium, zinc, magnesium, mercury, aluminum, gallium, indium, thallium, or mixtures thereof, and X is oxygen, sulfur, selenium, tellurium, nitrogen, phosphorus, arsenic, antimony, or mixtures thereof.

The semiconductor forming the core of the nanocrystal can include Group II-VI compounds, Group II-V compounds, Group III-VI compounds, Group III-V compounds, Group IV-VI compounds, Group I-III-VI compounds, Group II-IV-VI compounds, and Group II-IV-V compounds, for example, ZnS, ZnSe, ZnTe, CdS, CdSe, CdTe, HgS, HgSe, HgTe, MN, AlP, AlAs, AlSb, GaN, GaP, GaAs, GaSb, GaSe, InN, InP, InAs, InSb, TlN, TlP, TlAs, TlSb, PbS, PbSe, PbTe, or mixtures thereof.

The core can have an overcoating on a surface of the core. The overcoating can be a semiconductor material having a composition different from the composition of the core. The overcoat of a semiconductor material on a surface of the nanocrystal can include a Group II-VI compounds, Group II-V compounds, Group III-VI compounds, Group III-V compounds, Group IV-VI compounds, Group I-III-VI compounds, Group II-IV-VI compounds, and Group II-IV-V compounds, for example, ZnS, ZnSe, ZnTe, CdS, CdSe, CdTe, HgS, HgSe, HgTe, MN, AlP, AlAs, AlSb, GaN, GaP, GaAs, GaSb, GaSe, InN, InP, InAs, InSb, TlN, TlP, TlAs, TlSb, PbS, PbSe, PbTe, or mixtures thereof. The overcoating material can have a band gap greater than the band gap of the core material. Alternatively, the overcoating material can have a band (i.e. the valence band or the conduction band) intermediate in energy to the valence and conduction bands of the core material. See for example, U.S. Patent Application Publication No. 20040110002 titled, "Semiconductor Nanocrystal Heterostructures", which is incorporated by reference in its entirety.

The emission from the nanocrystal can be a narrow Gaussian emission band that can be tuned through the complete wavelength range of the ultraviolet, visible, or infrared regions of the spectrum by varying the size of the nanocrystal, the composition of the nanocrystal, or both. For example, CdSe can be tuned in the visible region and InAs can be tuned in the infrared region.

The population of nanocrystals can have a narrow size distribution. The population can be monodisperse and can exhibit less than a 15% rms deviation in diameter of the nanocrystals, preferably less than 10%, more preferably less than 5%. Spectral emissions in a narrow range of between 10 and 100 nm full width at half max (FWHM) can be observed. Semiconductor nanocrystals can have emission quantum efficiencies of greater than 2%, 5%, 10%, 20%, 40%, 60%, 70%, or 80%.

Methods of preparing semiconductor nanocrystals include pyrolysis of organometallic reagents, such as dimethyl cadmium, injected into a hot, coordinating agent. This permits discrete nucleation and results in the controlled growth of macroscopic quantities of nanocrystals. Preparation and manipulation of nanocrystals are described, for example, in U.S. Pat. No. 6,322,901, incorporated herein by reference in its entirety. The method of manufacturing a nanocrystal is a colloidal growth process and can produce a monodisperse particle population. Colloidal growth occurs by rapidly injecting an M donor and an X donor into a hot coordinating agent. The injection produces a nucleus that can be grown in a controlled manner to form a nanocrystal. The reaction mixture can be gently heated to grow and anneal the nanocrystal. Both the average size and the size distribution of the nanocrystals in a sample are dependent on the growth temperature. The growth temperature necessary to maintain steady growth increases with increasing average crystal size. The nanocrystal is a member of a population of nanocrystals. As a result of the discrete nucleation and controlled growth, the population of nanocrystals obtained has a narrow, monodisperse distribution of diameters. The monodisperse distribution of diameters can also be referred to as a size. The process of controlled growth and annealing of the nanocrystals in the coordinating agent that follows nucleation can also result in uniform surface derivatization and regular core structures. As the size distribution sharpens, the temperature can be raised to maintain steady growth. By adding more M donor or X donor, the growth period can be shortened.

An overcoating process is described, for example, in U.S. Pat. No. 6,322,901, incorporated herein by reference in its entirety. By adjusting the temperature of the reaction mixture during overcoating and monitoring the absorption spectrum of the core, over coated materials having high emission quantum efficiencies and narrow size distributions can be obtained.

The M donor can be an inorganic compound, an organometallic compound, or elemental metal. The inorganic compound M-containing salt can be a metal halide, metal carboxylate, metal carbonate, metal hydroxide, or metal diketonate, such as a metal acetylacetonate. See, for example, U.S. Pat. No. 6,576,291, which is incorporated by reference in its entirety. M is cadmium, zinc, magnesium, mercury, aluminum, gallium, indium or thallium. The X donor is a compound capable of reacting with the M donor to form a material with the general formula MX. Typically, the X donor is a chalcogenide donor or a pnictide donor, such as a phosphine chalcogenide, a bis(silyl) chalcogenide, dioxygen, an ammonium salt, or a tris(silyl)pnictide. Suitable X donors include dioxygen, bis(trimethylsilyl)selenide (($TMS)_2Se$), trialkyl phosphine selenides such as (tri-n-octylphosphine)selenide (TOPSe) or (tri-n-butylphosphine)selenide (TBPSe), trialkyl phosphine tellurides such as (tri-n-octylphosphine)telluride (TOPTe) or hexapropylphosphorustriamide telluride (HPPTTe), bis(trimethylsilyl)telluride (($TMS)_2Te$), bis(trimethylsilyl)sulfide (($TMS)_2S$), a trialkyl phosphine sulfide such as (tri-n-octylphosphine) sulfide (TOPS), an ammonium salt such as an ammonium halide (e.g., $NH_4Cl$), tris(trimethylsilyl)phosphide (($TMS)_3P$), tris(trimethylsilyl)arsenide (($TMS)_3As$), or tris(trimethylsilyl)antimonide (($TMS)_3Sb$). In certain embodiments, the M donor and the X donor can be moieties within the same molecule.

Size distribution during the growth stage of the reaction can be estimated by monitoring the absorption line widths of the particles. Modification of the reaction temperature in response to changes in the absorption spectrum of the particles allows the maintenance of a sharp particle size distribution during growth. Reactants can be added to the nucleation solution during crystal growth to grow larger crystals. By stopping growth at a particular nanocrystal average diameter, a population having an average nanocrystal diameter of less than 150 Å can be obtained. A population of nanocrystals can have an average diameter of 15 Å to 125 Å.

The particle size distribution can be further refined by size selective precipitation with a poor solvent for the nanocrystals, such as methanol/butanol as described in U.S. Pat. No. 6,322,901, incorporated herein by reference in its entirety.

For example, nanocrystals can be dispersed in a solution of 10% butanol in hexane. Methanol can be added dropwise to this stirring solution until opalescence persists. Separation of supernatant and flocculate by centrifugation produces a precipitate enriched with the largest crystallites in the sample. This procedure can be repeated until no further sharpening of the optical absorption spectrum is noted. Size-selective precipitation can be carried out in a variety of solvent/nonsolvent pairs, including pyridine/hexane and chloroform/methanol. The size-selected nanocrystal population can have no more than a 15% rms deviation from mean diameter, preferably 10% rms deviation or less, and more preferably 5% rms deviation or less.

The outer surface of the nanocrystal can include compounds derived from the coordinating solvent used during the growth process. The surface can be modified by repeated exposure to an excess of a competing coordinating group. For example, a dispersion of the capped nanocrystal can be treated with a coordinating organic compound, such as pyridine, to produce crystallites which disperse readily in pyridine, methanol, and aromatics but no longer disperse in aliphatic solvents. Such a surface exchange process can be carried out with any compound capable of coordinating to or bonding with the outer surface of the nanocrystal, including, for example, phosphines, thiols, amines and phosphates. The nanocrystal can be exposed to short chain polymers which exhibit an affinity for the surface and which terminate in a moiety having an affinity for a suspension or dispersion medium. Such affinity improves the stability of the suspension and discourages flocculation of the nanocrystal. Nanocrystal coordinating compounds are described, for example, in U.S. Pat. No. 6,251,303, which is incorporated by reference in its entirety.

More specifically, the coordinating ligand can have the formula:

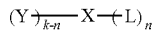

wherein k is 2, 3 or 5, and n is 1, 2, 3, 4 or 5 such that k-n is not less than zero; X is O, S, S=O, $SO_2$, Se, Se=O, N, N=O, P, P=O, As, or As=O; each of Y and L, independently, is aryl, heteroaryl, or a straight or branched $C_{2-12}$ hydrocarbon chain optionally containing at least one double bond, at least one triple bond, or at least one double bond and one triple bond. The hydrocarbon chain can be optionally substituted with one or more $C_{1-4}$ alkyl, $C_{2-4}$ alkenyl, $C_{2-4}$ alkynyl, $C_{1-4}$ alkoxy, hydroxyl, halo, amino, nitro, cyano, $C_{3-5}$ cycloalkyl, 3-5 membered heterocycloalkyl, aryl, heteroaryl, $C_{1-4}$ alkylcarbonyloxy, $C_{1-4}$ alkyloxycarbonyl, $C_{1-4}$ alkylcarbonyl, or formyl. The hydrocarbon chain can also be optionally interrupted by —O—, —S—, —N($R^a$)—, —N($R^a$)—C(O)—O—, —O—C(O)—N($R^a$)—, —N($R^a$)—C(O)—N($R^b$)—, —O—C(O)—O—, —P($R^a$)—, or —P(O)($R^a$)—. Each of $R^a$ and $R^b$, independently, is hydrogen, alkyl, alkenyl, alkynyl, alkoxy, hydroxylalkyl, hydroxyl, or haloalkyl.

An aryl group is a substituted or unsubstituted cyclic aromatic group. Examples include phenyl, benzyl, naphthyl, tolyl, anthracyl, nitrophenyl, or halophenyl. A heteroaryl group is an aryl group with one or more heteroatoms in the ring, for instance furyl, pyiridyl, pyrrolyl, phenanthryl.

Other coordinating ligands are described in, for example, U.S. Pat. Nos. 6,319,426; 6,306,610; 6,921,496; 7,160,613; 7,190,870; and 7,229,690, each of which is incorporated by reference in its entirety.

A suitable coordinating ligand can be purchased commercially or prepared by ordinary synthetic organic techniques, for example, as described in J. March, *Advanced Organic Chemistry*, which is incorporated by reference in its entirety.

Transmission electron microscopy (TEM) can provide information about the size, shape, and distribution of the nanocrystal population. Powder X-ray diffraction (XRD) patterns can provided the most complete information regarding the type and quality of the crystal structure of the nanocrystals. Estimates of size are also possible since particle diameter is inversely related, via the X-ray coherence length, to the peak width. For example, the diameter of the nanocrystal can be measured directly by transmission electron microscopy or estimated from X-ray diffraction data using, for example, the Scherrer equation. It also can be estimated from the UV/Vis absorption spectrum.

EXAMPLES

The $\lambda$=514 nm line of an Ar-ion laser was used as the excitation source with a typical intensity of ~20 W/cm². Images were taken using a 100× oil immersion objective (Nikon, Plan Apo) and an intensified CCD Camera (Pentamax, Princeton Instruments). The method used standard epifluorescence video imaging (as shown in FIG. 1) in off-focus mode and allows the tracking of particles with 100 ms temporal resolution.

Primary bovine aortic endothelial cells (BAEC-77, passage 10-15) were cultured in DMEM supplemented with 10% fetal calf serum, 1% L-glutamine, and 1% penicillin-streptomycin. Before seeding, cell culture flasks and glass slides were coated with 0.2% gelatin at room temperature. Microfluidic chambers (from Ibidi) were coated with fibronectin to promote cell attachment in micro-environment. Cell cultures were kept in a humidified incubator maintained at 37° C., with 5% $CO_2$ and 95% air.

Three sets of CdSe/ZnS (core/shell) nanocrystals were used in the experiments, NC655, NC605 and NC565 with the emission wavelength centered around $\lambda$=655 nm, 605 nm and 565 nm respectively. NC655 nanocrystals coated with streptavidin were from Quantum Dot Corporation; NC605 nanocrystals coated with IgG were from Invitrogen; NC565 nanocrystals coated with PEG-OH were synthesized in lab.

Figure 7A:
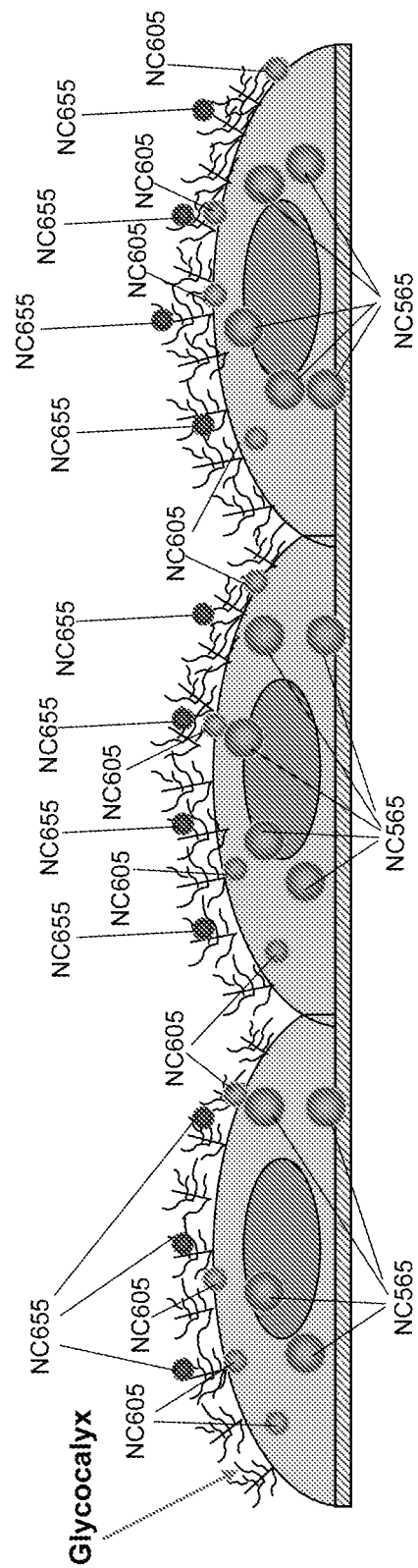
FIG. 7A is a schematic illustration of labeled cells.

After cell monolayers reached confluence, three layers of nanocrystals were attached to the cell as shown in FIG. 7A. Cells were incubated in culture medium with 5 nM NC565 for 15 min at 37° C. to allow the nanocrystals to be incorporated into intracellular vesicles via endocytosis. After five quick rinses in DPBS to remove excessive nanocrystals in solution, cells were chilled on ice for 10 min and blocked with 2% goat serum and 2% BSA for 20 min to reduce nonspecific background staining. To label the heparan sulfate glycosaminoglycans (HSGAG) in the glycocalyx layer, cells were incubated with 5 μg/mL heparan sulfate biotin antibody (US Biological) for 20 min and washed three times with DPBS. Cells were subsequently incubated with 2 nM NC655 for 15 min, and later washed with DPBS. After completing glycocalyx staining, cells were washed three times and incubated with 30 μg/ml PECAM-1 IgG antibody (AbD Serotec) to for 15 min Finally, QD605 were added in a final concentration of 2 nM to stain platelet/endothelial cell adhesion molecule 1 (PECAM-1, same as CD31). The cell labeling procedure was performed on ice so as to limit nanocrystal endocytosis during the incubation procedure, with the exception of NC565. Prepared cell samples were transferred onto the nanopositioning stage (Physik Instrumente, P-527) and imaged immediately at room temperature.

FIG. 7A is a schematic illustration of nanocrystal labeling of endothelial cells. Intracellular vesicles (NC565, in green), membrane PECAM-1 (NC605, in orange), and glycocalyx (NC655, in red) were labeled as described above. NC565 were added in the growth medium to be taken up by cells through endocytocis; NC605-IgG particles adhered to antibody attached PECAM molecules through IgG interaction; and NC655-streptavidin recognized biotin-coated heparin sulfate glycosaminoglycan antibody.

Figure 7B:
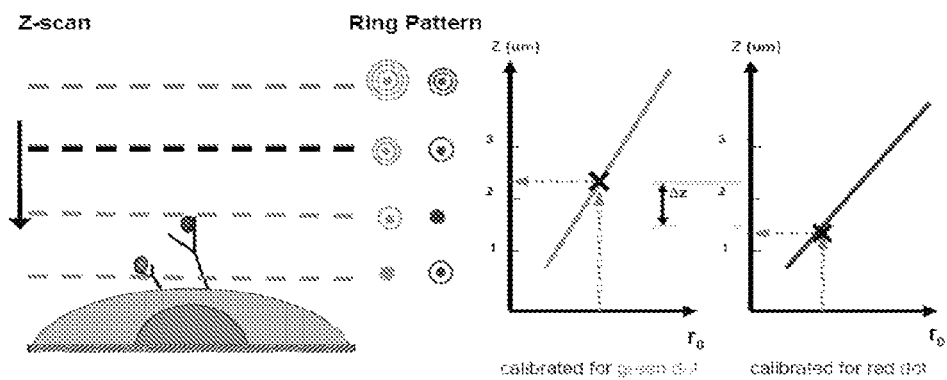
FIG. 7B is a schematic diagram depicting how cell labels, $r_0$ and z-displacement are related.
Figure 8:
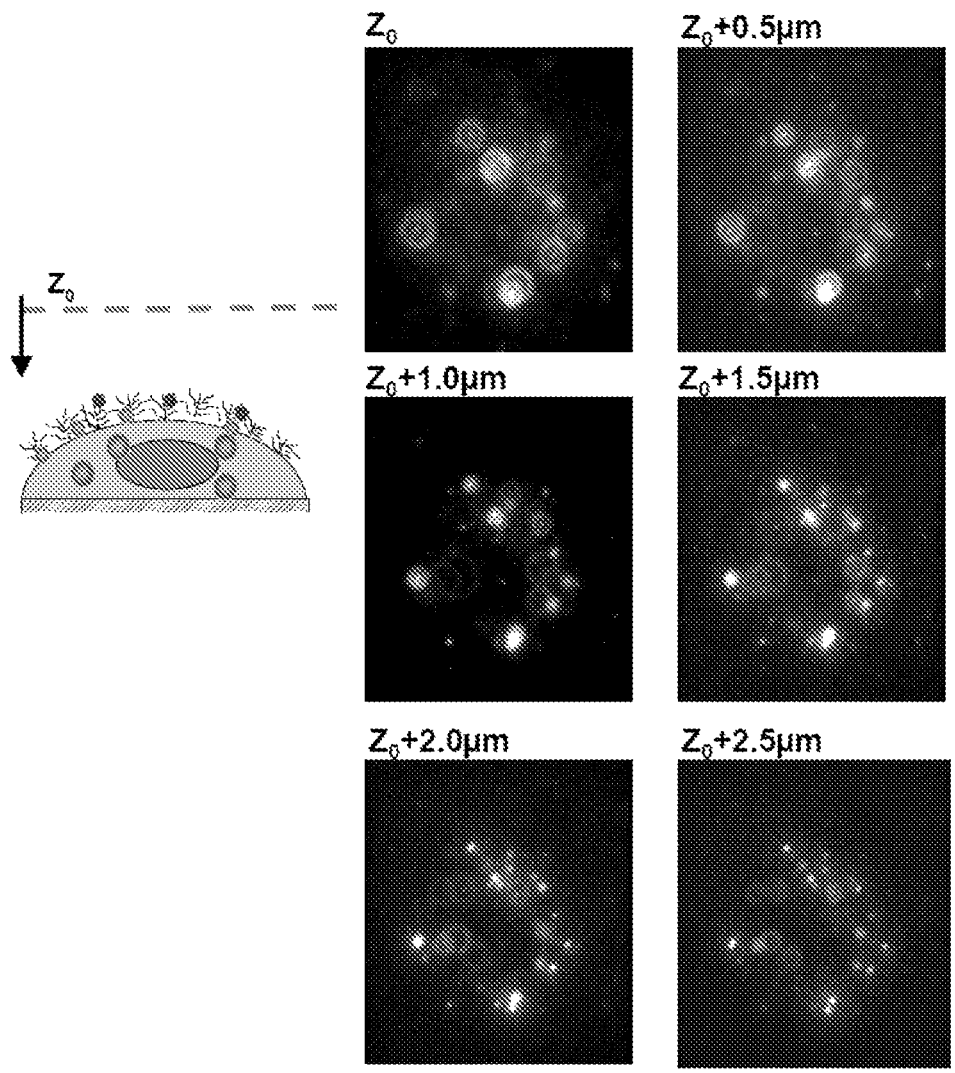
FIG. 8 is a series fluorescence microscope images of labeled cells at varying z-displacements.

Individual cells were first identified with NC565 signals, and thus images for PECAM-associated nanocrystals and Glycocalyx-associated nanocrystals on the same cell could be recorded by switching emission spectrum filters. Once a cell had been properly selected, the stage was locked in x- and y-position. The nano-positioner was then placed to a reference position so that the focal plane of the objective fell in the medium just outside the cell body. The camera was set to capture images at a frame rate of 5 Hz. As the stage was moved such that the focal plane moved toward and through the cell, ring patterns of the nanocrystal emission change accordingly and nanocrystals at deeper z-positions start to appear. See FIG. 7B. FIG. 8 gives an example of approximately ten NC565-containing vesicles detected in one cell as the objective scanned through the cell body. After completing the collection of NC565 signal, the emission filter was switched and the procedure repeated to collect with NC605 and NC655 data.

Figure 9:
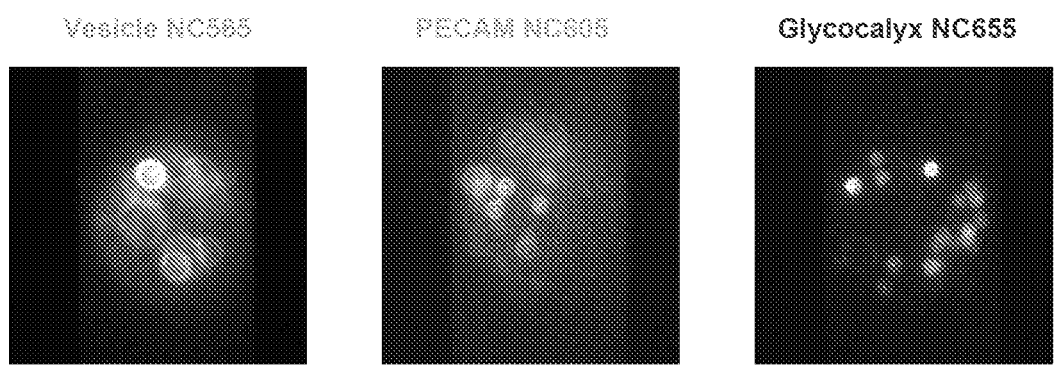
FIG. 9 is a series fluorescence microscope images of labeled cells at a fixed z-displacement, recorded with different emission wavelength filters in place.

When images at the three different wavelengths, recorded at the same z-position are compared (FIG. 9), the ring patterns indicate that vesicles (NC565) were the furthest from the scanning plane while the glycocalyx (NC655) was the closest to the scanning plane. The relative positions of the three layers from the data corroborated with the cell structure, i.e., the glycocalyx being the outermost layer and the vesicles being located inside the cell.

Figure 10A:
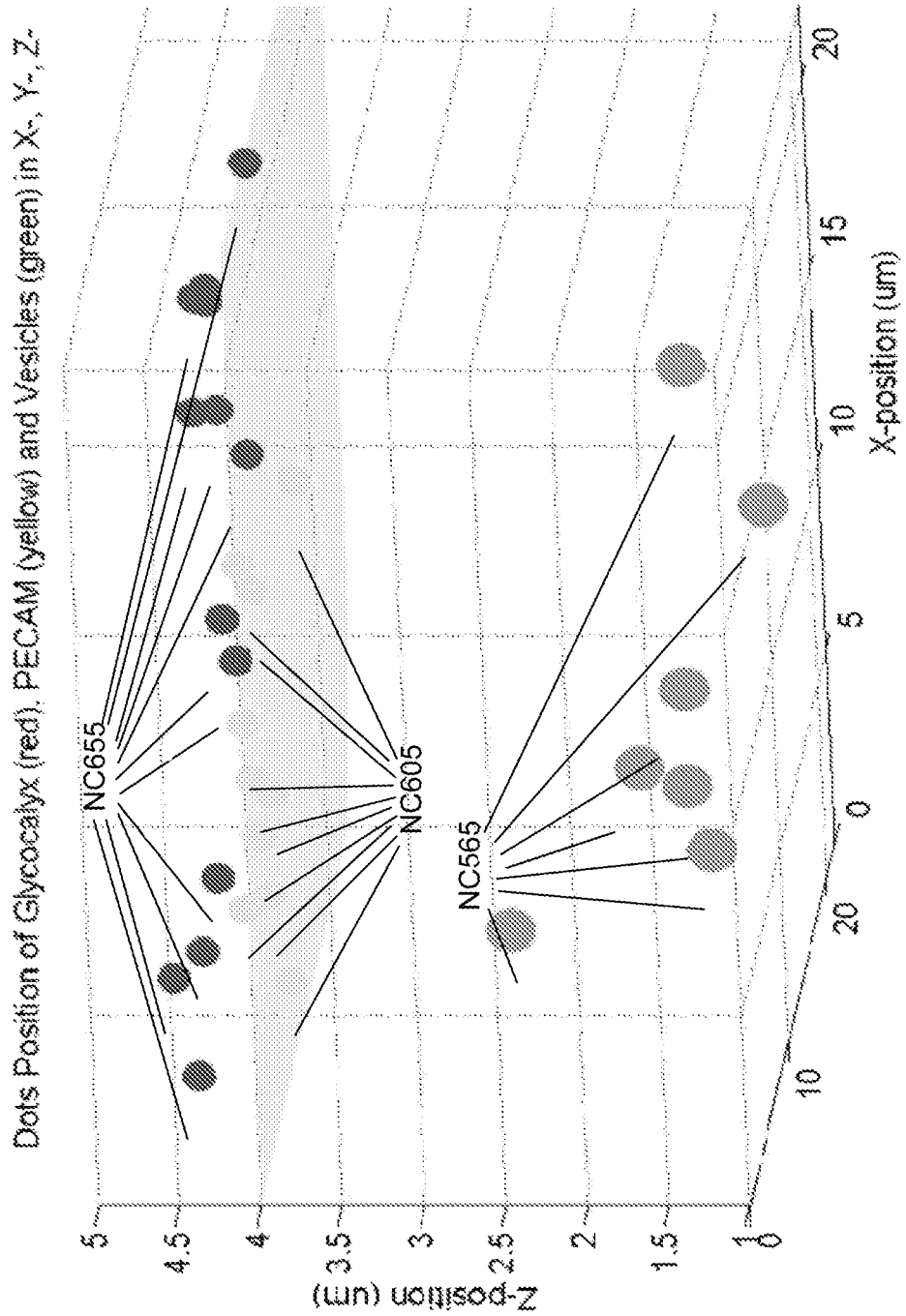
FIGS. 10A-10B are graphs depicting relative locations of nanocrystals on a labeled cell.
Figure 10B:
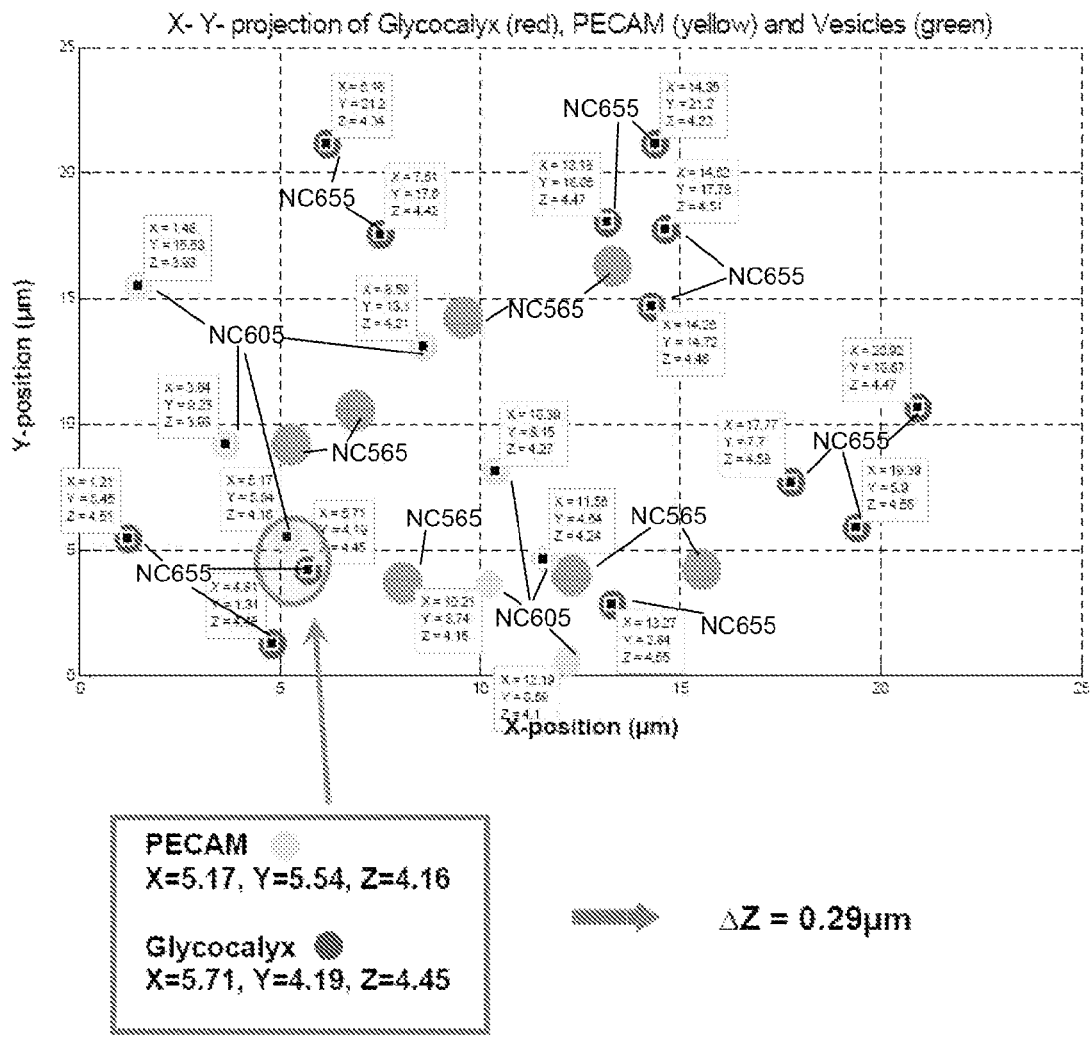

After data processing, the precise location of each nanocrystal can be determined. The x,y location is calculated by a Gaussian fitting of the central spot, and z position from correlating the ring radius to the calibration curve. By this method, precise locations of seven vesicle-associated nanocrystals, eight PECAM-associated nanocrystals, and thirteen glycocalyx-associated nanocrystals, associated with a single cell were determined (FIGS. 10A-10B). The maximum z-distance between vesicle-associated nanocrystals and glycocalyx-associated nanocrystals was roughly 3.5 µm, on the same order as known cell body height. Inserting a reference plane at z=4 µm (transparent blue) near the PECAM-associated nanocrystals (yellow marker), the glycocalyx-associated nanocrystals (red marker) were distinguished as being located generally on the extracellular side of the membrane.

With the glycocalyx layer mapped in 3D space, the thickness of the layer can be estimated by comparing the relative distance between the glycocalyx-associated nanocrystals and the membrane. Two possible approaches are discussed below.

The glycocalyx thickness can be obtained directly from the z-difference of a glycocalyx-PECAM nanocrystal pair, assuming the membrane roughness between the two nanocrystals in the pair is negligible. A close examination of all the nanocrystals mapped (FIGS. 10A-B) revealed one glycocalyx-PECAM pair that satisfied the criteria. The PECAM-associated nanocrystal in this pair, as highlighted in FIG. 10B right panel, was located at x=5.17 µm, y=5.54 µm and z=4.16 µm; while the glycocalyx-associated nanocrystal was located at x=5.71 µm, y=4.19 µm and z=4.45 µm. Assuming the PECAM-associated nanocrystal was close enough to the glycocalyx-associated nanocrystal in the x,y plane, the z-difference between the two, $\Delta z=0.29$ µm, provided an estimate of the glycocalyx thickness at this location.

Figure 11:
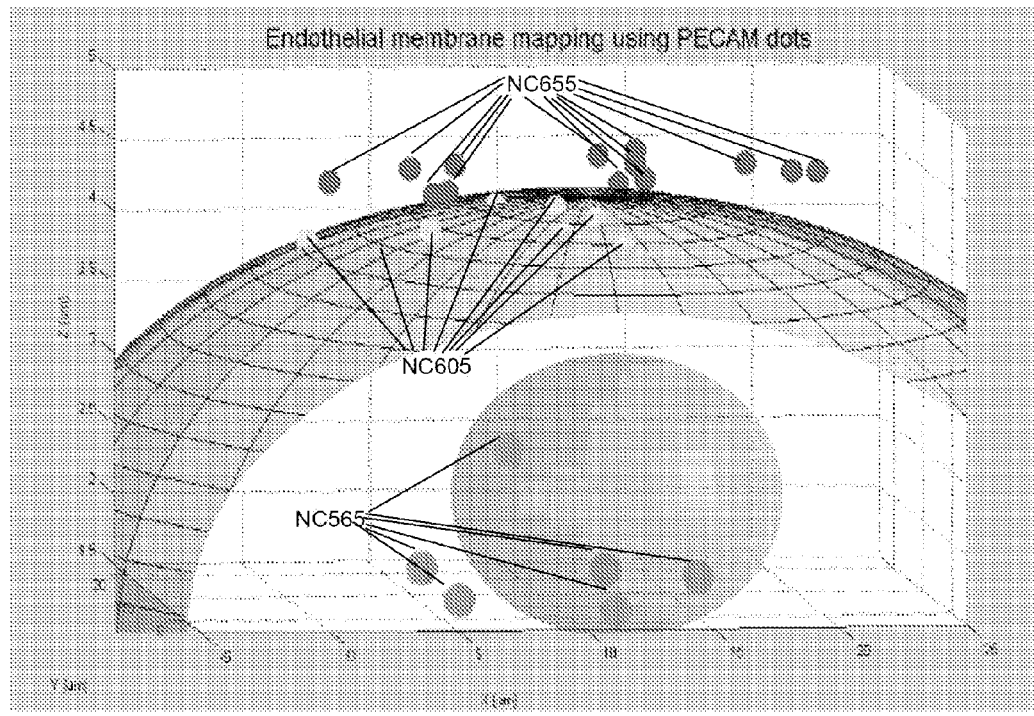
FIG. 11 is a graph depicting relative locations of nanocrystals and models of cellular structures on a labeled cell.

A second method involves assuming an ellipsoidal shape for the cell body, consistent with reported AFM measurements, and simulating a continuous surface of cell membrane by fitting the positions of eight PECAM-associated nanocrystals to an ellipsoidal surface as illustrated in FIG. 11. The parameters of the ellipsoid fell within the physical range of cell geometry. Therefore, the z-distance of each individual glycocalyx-associated nanocrystal above membrane was calculated by comparing it to the z-position of the membrane right beneath the nanocrystal (i.e., at the same x,y position). The mean of the $\Delta z$ yielded an estimate of average glycocalyx thickness on the cell of 0.35±0.17 µm, which was on the same order of magnitude of the result from method 1.

Figure 12:
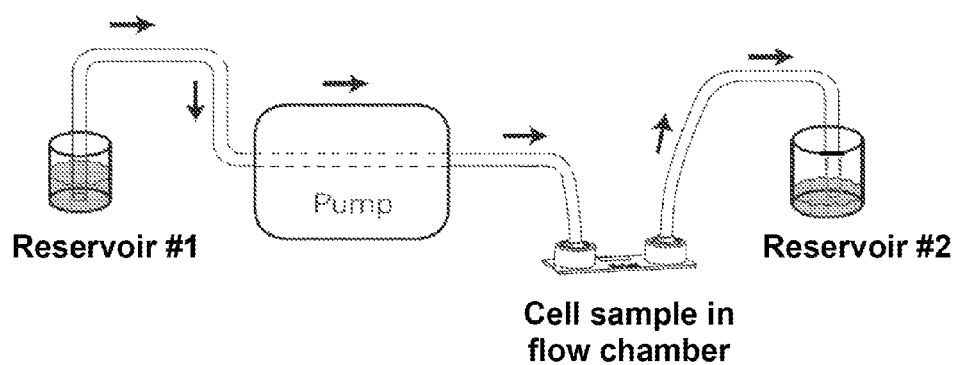
FIG. 12 is a schematic diagram depicting a flow cell.
Figure 13A:
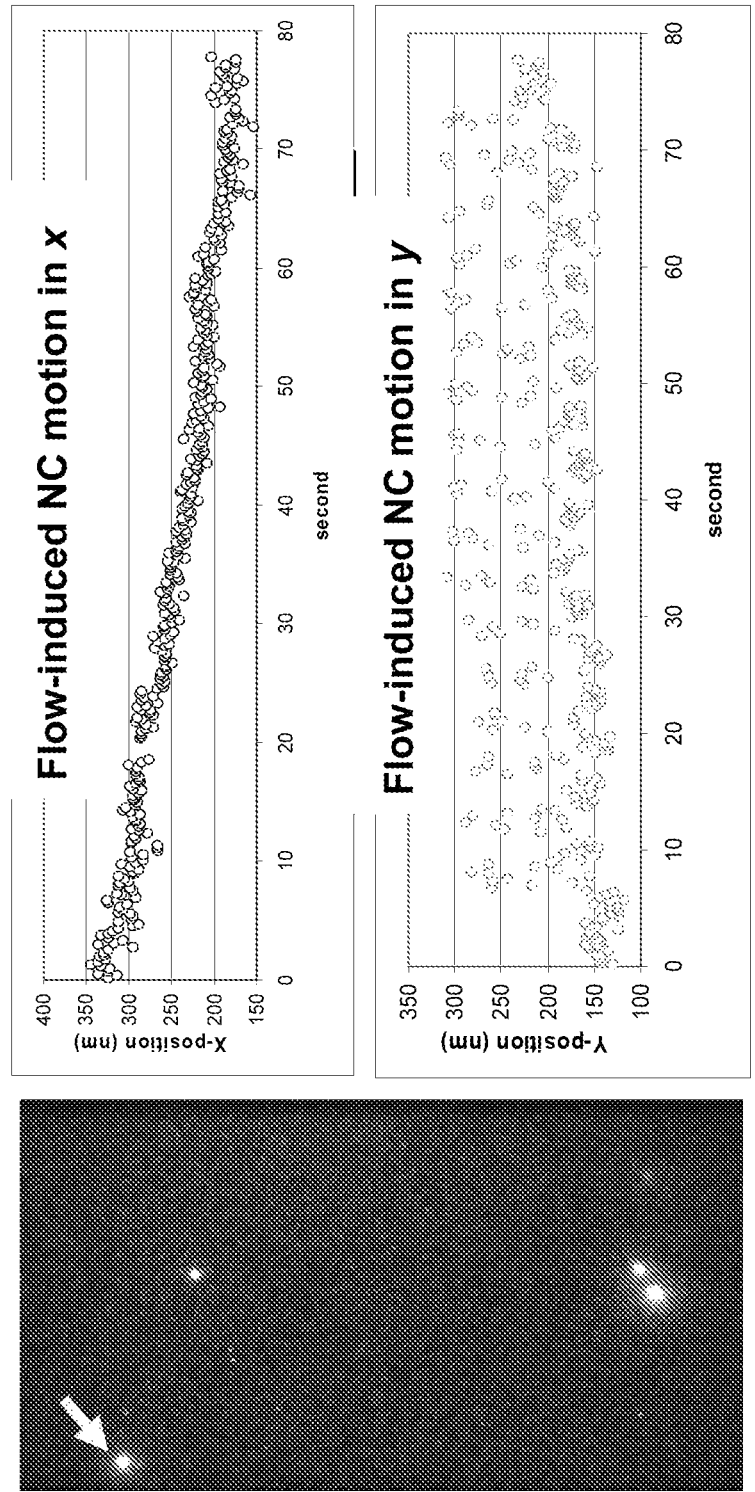
FIG. 13A is a fluorescence microscope image and graphs depicting time-dependent positions of a nanocrystal.
Figure 13B:
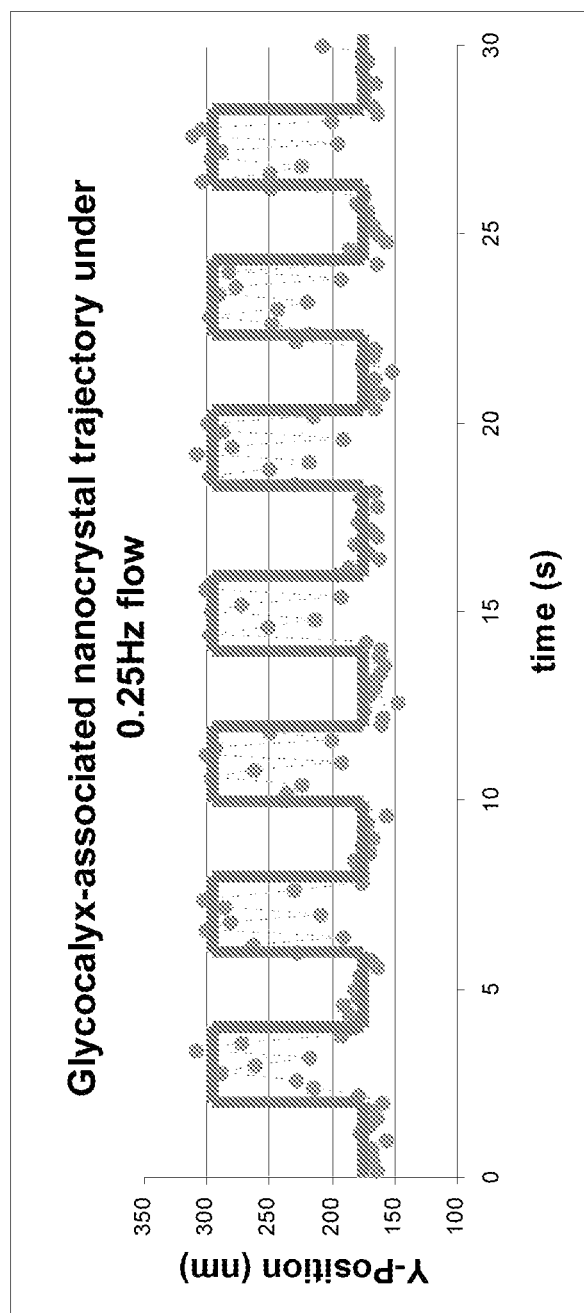
FIG. 13B is a graph depicting time-dependent positions of a nanocrystal.

In a related application, the shear modulus of the glycocalyx was determined Using the system depicted in FIG. 12, BAEC were subjected to periodic shear flows (0.25 Hz). The glycocalyx was labeled with nanocrystals as described above. FIG. 13A shows an image recorded using the system of FIG. 12. The time dependent x- and y-positions of the nanocrystal highlighted by the yellow arrow are shown in the graphs at right. FIG. 13B shows a detail of the y-position data, with the time trace of applied flow overlaid (orange line). Displacements of the nanocrystal closely match the applied flow. Average displacement was 108±77 nm. The applied shear stress was calculated to be 15 dyne/cm$^2$, based on the fluid flow and chamber dimensions. Preliminary estimates of the shear modulus of the glycocalyx were in the range 3.7 Pa to 7.5 Pa. For comparison, the cell itself has a shear modulus on the order of 50 Pa to 600 Pa, depending on the method used.

Figure 14:
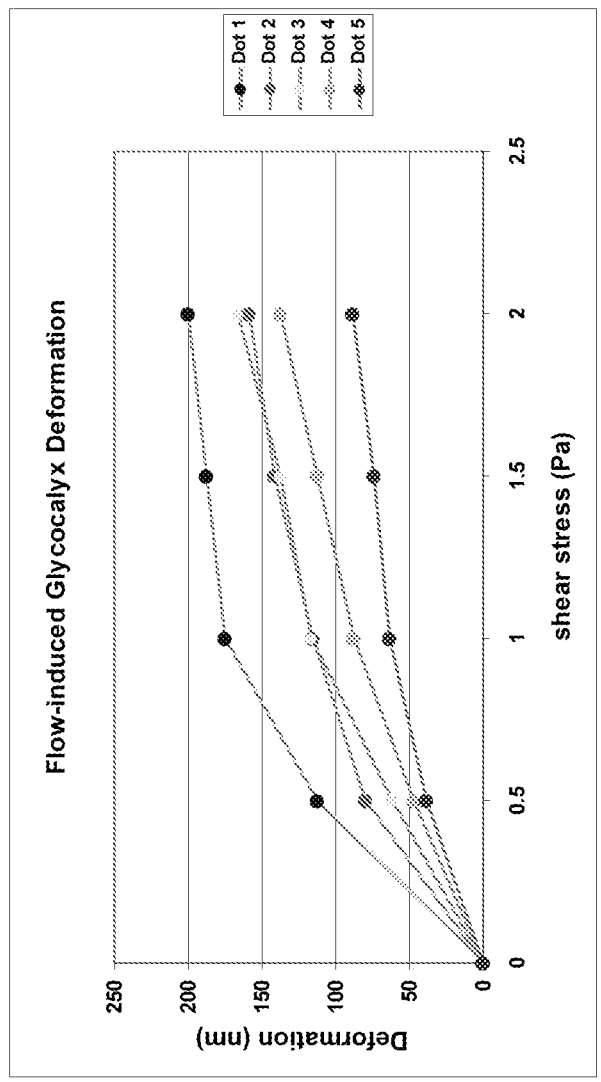
FIG. 14 is a graph depicting the relationship between shear stress applied in a flow cell and nanocrystal displacement.

FIG. 14 shows data illustrating the relationship between shear stress and nanocrystal displacement for five different nanocrystals. From this information, the shear modulus G for the glycocalyx was determined to be to be 6.7±3.3 Pa.

Other embodiments are within the scope of the following claims.

What is claimed is:

1. A method of imaging a microscopic object comprising:
arranging a microscopic object associated with at least a first and a second semiconductor nanocrystal in the optical field of an optical microscope, wherein at least one of the semiconductor nanocrystals has a coating that has an affinity for a biological structure;
recording a first fluorescence image of the first and second semiconductor nanocrystals at a first focal depth;
recording a second fluorescence image of the first and second semiconductor nanocrystals at a second focal depth different from the first focal depth; and
calculating the relative depths of the first and second semiconductor nanocrystals based at least in part on the first and second fluorescence images,
wherein calculating the relative depths of the first and second semiconductor nanocrystals includes measuring a radius of the first semiconductor nanocrystal as it appears in each of the first and second fluorescence images, wherein measuring the radius includes determining a radial intensity profile, and wherein determining the radial intensity profile includes calculating an integrated radial intensity profile for a plurality of different angles.

2. The method of claim 1, further comprising fitting the radial intensity profile with one or more Gaussian curves.

3. The method of claim 1, wherein measuring the radius includes measuring a radius at a plurality of different angles.

4. The method of claim 1, further comprising fitting the radial intensity profile with one or more Gaussian curves.

5. The method of claim 1, further comprising correlating the measured radius of the first semiconductor nanocrystal with the relative depth of the first semiconductor nanocrystal.

6. The method of claim 1, further comprising determining relative three-dimensional coordinates of the first and second semiconductor nanocrystals based at least in part on the first and second fluorescence images.

7. The method of claim 6, further comprising determining a three-dimensional shape of the object based at least in part on the relative three-dimensional coordinates of the first and second semiconductor nanocrystals.

8. The method of claim 1, wherein the object includes a biological structure.

9. The method of claim 8, wherein the biological structure includes a cell.

10. The method of claim 8, wherein the first semiconductor nanocrystal is associated with a moiety having a specific affinity for a biomolecule.

11. The method of claim 1, further comprising tracking the location of at least one semiconductor nanocrystal as a function of time.

12. The method of claim 11, wherein tracking the location includes determining three-dimensional coordinates for the semiconductor nanocrystal.

* * * * *